(12) United States Patent
Kofoed

(10) Patent No.: US 7,717,917 B2  
(45) Date of Patent: May 18, 2010

(54) ANCILLARY DEVICE FOR POSITIONING A BONE GRAFT IN A JOINT IN ORDER TO ENSURE ARTHRODESIS OF THE JOINT

(75) Inventor: Hakon Kofoed, Charlottenlund (DK)

(73) Assignee: Newdeal, Lyons (FR)

( * ) Notice: Subject to any disclaimer, the term of this patent is extended or adjusted under 35 U.S.C. 154(b) by 902 days.

(21) Appl. No.: 11/220,172

(22) Filed: Sep. 6, 2005

(65) Prior Publication Data

US 2006/0058805 A1 Mar. 16, 2006

(30) Foreign Application Priority Data

Sep. 6, 2004 (FR) .................. 04 09427  
Sep. 6, 2004 (FR) .................. 04 09428

(51) Int. Cl.  
*A61B 17/56* (2006.01)

(52) U.S. Cl. .................. 606/86 R

(58) Field of Classification Search .......... 623/13.17, 623/20.17, 13.11–13.12  
See application file for complete search history.

(56) References Cited

U.S. PATENT DOCUMENTS

| 4,877,020 | A | 10/1989 | Vich ................ 128/92 |
| 6,228,022 | B1 | 5/2001 | Friesem et al. ........ 600/204 |
| 2002/0032447 | A1 | 3/2002 | Weikel et al. |
| 2004/0087956 | A1 | 5/2004 | Weikel et al. |
| 2004/0133208 | A1 | 7/2004 | Weikel et al. |

FOREIGN PATENT DOCUMENTS

| AU | 1457900 A | 5/2000 |
| AU | 8374901 A | 3/2002 |
| AU | 8692401 A | 3/2002 |
| BR | 0113680 A | 6/2004 |
| CA | 2420688 A1 | 3/2002 |
| CN | 1449262 | 10/2003 |
| DE | 3505567 A1 | 6/1986 |
| EP | 0153831 A2 * | 9/1985 |
| EP | 1124495 A2 | 8/2001 |
| EP | 1408841 A1 | 4/2004 |
| ES | 283078 U | 5/1985 |
| JP | 61135652 A | 6/1986 |
| JP | 2002528163 T | 9/2002 |
| JP | 2004514470 T | 5/2004 |
| WO | WO 0024326 A2 | 5/2000 |
| WO | WO 0217794 A1 | 3/2002 |
| WO | WO 0219930 A2 | 3/2002 |
| ZA | 200301517 A | 3/2004 |

* cited by examiner

*Primary Examiner*—Eduardo C Robert  
*Assistant Examiner*—Elana B Fisher  
(74) *Attorney, Agent, or Firm*—Thomas, Kayden, Horstemeyer & Risley, LLP

(57) ABSTRACT

An ancillary device for positioning a bone graft between bones separated by an articular slot, to ensure arthrodesis of a joint, wherein the bone graft is placed in a recess provided at the end of one or more bones defining the articular slot, and comprising means for driving the bone graft, provided with support means on the bone graft suitable for moving the latter in the recess, and actuation means, functionally connected to the driving means, and capable of being handled in order to control the movement of the bone graft.

24 Claims, 4 Drawing Sheets

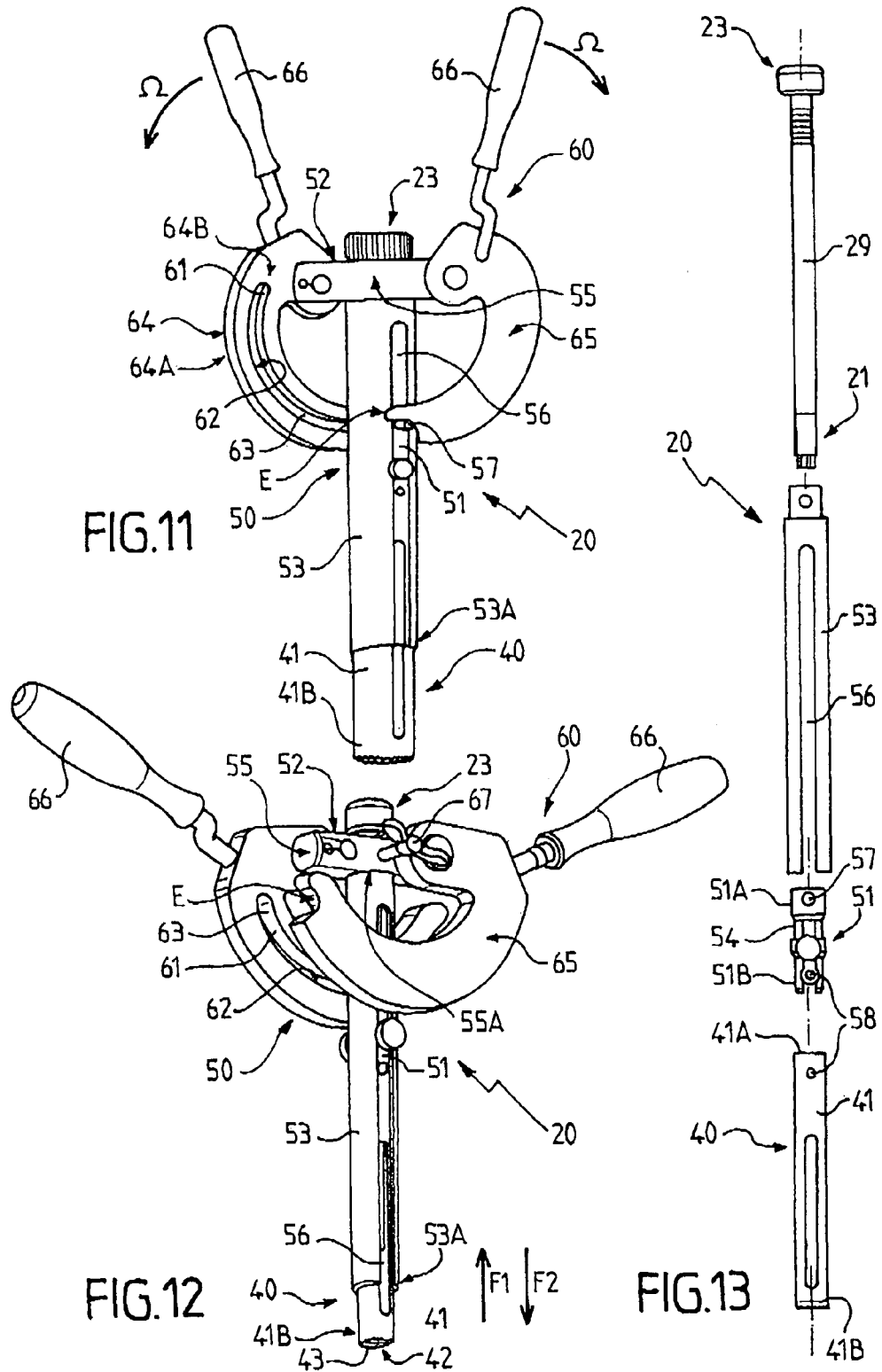

ANCILLARY DEVICE FOR POSITIONING A BONE GRAFT IN A JOINT IN ORDER TO ENSURE ARTHRODESIS OF THE JOINT

CROSS-REFERENCE TO RELATED APPLICATION

This Application claims priority to copending French Patent Application entitled, "Fixation Implant For a Bone Graft Within a Joint for the Purpose of Ensuring Arthrodesis of the Joint," having Application No. FR-04 09427, filed on Sep. 6, 2004, and copending French Patent Application entitled, "Ancillary Device For Positioning a Bone Graft in a Joint in Order to Ensure Arthrodesis of the Joint," having Application No. FR-04 09428, filed on Sep. 6, 2004, both of which are entirely incorporated herein by reference.

This invention relates to the general technical field of surgical accessories (referred to as "ancillary devices") to be used for arthrodesis.

This invention relates more specifically to an ancillary device for positioning a bone graft between at least a first and a second bone separated by an articular slot, in particular for arthrodesis of the joint.

This invention also relates to a method for arthrodesis of a joint between at least two bones separated by an articular slot.

The ancillary device for positioning according to the invention is specifically designed to be used for arthrodesis of a joint and, in particular, but not exclusively, the ankle joint.

An arthrodesis is a surgical intervention intended to almost entirely eliminate the mobility of a joint by causing a "bone fusion". Such a surgical intervention can be necessary when a patient is suffering from severe and final stage arthritis, or when the bone cartilage forming the joint is badly damaged.

To perform such interventions, it is known to resect the damaged cartilage surfaces of the joint so as to place into contact, by compression, the bone surfaces opposite the bones forming the joint, thus enabling osteosynthesis.

However, such a method can lead to a shortening of the limb concerned, which is obviously undesirable, not only from an aesthetic perspective, but also due to complications (excessive claudication, for example) that may result.

To overcome these disadvantages, it is known to form a recess on both sides of the articular slot by cutting bone fragments at the level of the extremities opposite the bones forming the joint. This recess, which is preferably cylindrical, is then filled with a bone graft such as a substantially cylindrical bone sample taken from the same patient, for example from the iliac crest.

This procedure thus enables the damaged cartilaginous surfaces to be removed and the damaged bone ends to be replaced with a healthy bone graft, without shortening the limb concerned. Then, the bone graft is attached to the bones forming the joint in order to enable osteosynthesis between the bone graft and the bones, thus ensuring the arthrodesis of the joint.

Although this latter method enables a beneficial result to be obtained in terms of immobilisation of the joint, while limiting the shortening phenomenon, nevertheless has some notable disadvantages.

First, such a method requires, in addition to the incision made at the level of the joint, an additional incision in another part of the patient's body in order to extract the bone graft which will then be transplanted to the area of the joint. However, in surgical interventions, it is important to limit the number of incisions made, in particular so as to reduce the risk of infection.

In addition, the extraction of the bone graft from another part of the body is also capable of causing other complications, during or after the operation.

Finally, the use of this method generally involves a rather long and difficult intervention for the patient.

The aims of the invention are therefore to overcome the various disadvantages listed above and to propose a new ancillary device for positioning a bone graft between at least a first and a second bone separated by an articular slot, in particular for arthrodesis of the joint, which enables precise and rapid positioning of the bone graft between the bones forming the joint in order to accelerate the osteosynthesis, and eliminates the need for the transplantation step.

Another aim of the invention is to propose a new ancillary positioning device which is easy to produce.

Another aim of the invention is to propose a new ancillary positioning device which is particularly easy and intuitive to handle and which allows for a rapid surgical intervention.

Another aim of the invention is to propose a new ancillary positioning device that holds the joint effectively and in a comfortable position.

Another aim of the invention is to propose a new ancillary positioning device enabling the positioning of the bone graft to be determined at any time in the operation, in particular during or after the cutting of the bone graft.

Another aim of the invention is to propose a new ancillary positioning device that makes it possible to avoid any risk of damage to the bone graft as it is being positioned.

Another aim of the invention is to propose a new ancillary positioning device that enables the means for cutting the bone graft to be removed easily, while holding the bone graft in position in the joint.

The invention also aims to propose a new method for arthrodesis of a joint using a bone graft placed between at least two bones of the joint, requiring only one incision.

Another aim of the invention is to propose a new arthrodesis method that is less invasive than the methods of the prior art.

Another aim of the invention is to propose a new arthrodesis method that enables the joint to be held effectively, without causing the limb concerned to be shortened.

Another aim of the invention is to propose a new arthrodesis method that is less distressing for the patient than the methods of the prior art.

Another aim of the invention is to propose a new arthrodesis method that is particularly easy to perform by the surgeon.

Another aim of the invention is to propose a new arthrodesis method enabling the bone graft to be immobilised quickly, and the osteosynthesis between the bone graft and the surrounding bones to be accelerated.

Another aim of the invention is to propose a new arthrodesis method that can be performed quickly and that requires a limited number of steps.

The aims of the invention are achieved by the ancillary device for positioning a bone graft 5 intended to be placed in a recess 6, 6', 6", 8 formed at the end of a first 2 and/or second 3 bone defining an articular slot 4, in particular for ensuring the arthrodesis of a joint 1, which ancillary device includes:
  support means 22 on the bone graft 5,
  actuating means 23, capable of being handled in order to control the movement of the bone graft 5, characterised in that it comprises
  means for driving 21 the bone graft 5 provided with said support means 22 suitable for moving said graft in the recess 6, 6', 6", 8,
  means 40 for in situ cutting of the graft 5 at the end of the first 2 and/or second 3 bone defining the articular slot 4, and in that the actuating means 23 are functionally connected to the driving means 21 and to the cutting means 40 in order to move the bone graft 5 in the recess 6, 6', 6", 8 in which said graft has been placed.

The aims of the invention are also achieved by a method for arthrodesis of a joint between at least two bones separated by an articular slot and including the following steps:

a step of cutting in situ at least one first bone fragment at the end of one of the two bones, referred to as the first bone, so that the first bone fragment has a bleeding bone surface and an articular surface, with said articular surface at least partially defining the articular slot, a step of moving in situ the first bone fragment so that at least one portion of its bleeding bone surfaces comes into contact with the other bone, referred to as the second bone, so as to enable the osteosynthesis of said first bone fragment with said second bone.

Other characteristics and advantages of the invention will be seen in greater detail in the description below, and in the appended drawings provided as illustrative and non-limiting examples, in which:

FIG. 11 is a perspective view showing the ancillary positioning device according to the invention provided with an instrument for removing the cutting means, in a pre-extraction position, prior to removal of the cutting means.

FIG. 12 is a perspective view showing the ancillary positioning device according to the invention provided with the extraction instrument in a post-extraction position, after removal of the cutting means.

FIG. 13 is a front cutaway view showing a detail of the ancillary positioning device according to the invention.

FIGS. 1 to 7 show three alternatives of a surgical method according to the invention for performing an arthrodesis of the ankle joint.

Arthrodesis of joint becomes necessary when the joint is in such a damaged condition that other less severe surgical interventions, such as, for example, those involving the placement of prostheses, would be ineffective. In this case, it becomes necessary to completely immobilise the joint. This invention is shown in the case of an ankle joint, but can be applied to any type of joint in a human or animal body.

A damaged joint is characterised in particular by the condition of the cartilage of the bones defining the articular slot. In the case of severe arthritis, this cartilage is particularly worn down and can cause pain or even inflammation of the joint.

Figure 1:
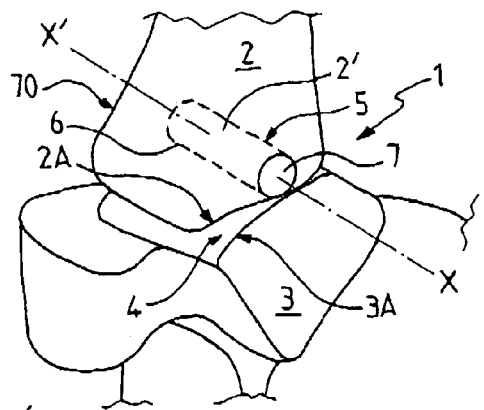
FIG. 1 is a perspective view showing an ankle joint with a bone graft formed by a single bone fragment, placed between the bones located on each side of the articular slot.
Figure 3:
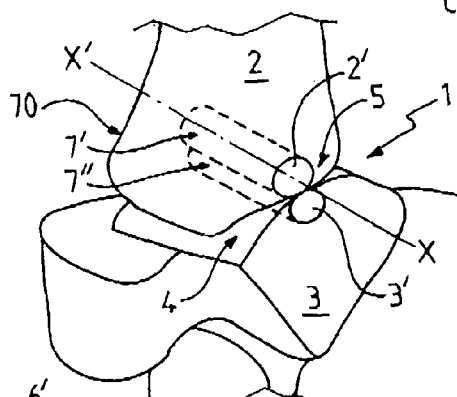
FIG. 3 is a perspective view showing an ankle joint with a bone graft formed by two bone fragments, placed between the bones located on each side of an articular slot.
Figure 5:
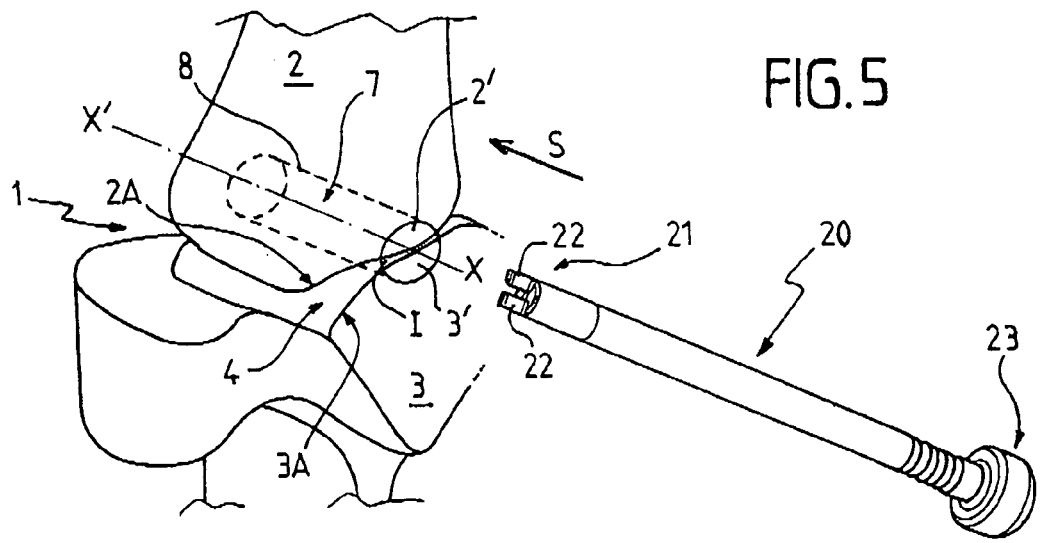
FIG. 5 is a perspective view showing an ankle joint with a bone graft, formed by two bone fragments, placed between the bones located on each side of an articular slot, as well as a detail of an ancillary positioning device according to the invention.

FIGS. 1, 3 and 5 show a joint 1 formed by at least two bones, namely a first bone 2 and a second bone 3 located on each side of an articular slot 4. However, the joint 1 could clearly include a third bone, for example, located between the first bone 2 and the second bone 3, without going beyond the scope of the invention. In the context of the invention, the term "articular slot" refers to the articular interface (or space), i.e. the narrow inter-articular space, in the form of a slot, that, before the intervention, separates the bones 2, 3 forming the joint 1.

Figures 2A, 2B:
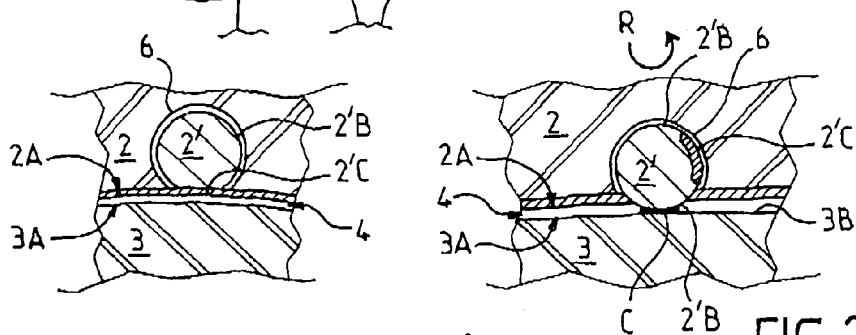
FIGS. 2a and 2b are cross-section detail views showing the bone graft shown in FIG. 1, in a position prior to its positioning (FIG. 2a) and a position following its positioning (FIG. 2b), referred to as functional position, in which the bone reconstruction and the osteosynthesis of the bone graft with the bones forming the joint can take place.

FIGS. 1, 2a and 2b show a first embodiment of an arthrodesis method according to the invention.

The method according to the invention thus comprises a first step in which an incision is made at the level of the joint 1. The method then comprises a step (a) of cutting at least one first bone fragment 2' at the end 2A of one of the two bones 2, 3, referred to as the first bone 2, so that the first bone fragment 2' comprises a bleeding bone surface 2'B and an articular surface 2'C, wherein said articular surface 2'C at least partially defines the articular slot 4. Thus, the articular surface 2'C corresponds to the cartilaginous surface of the first bone 2. In the context of the invention, the bleeding bone surface 2'B of the first bone fragment 2' corresponds to the surface on which the first bone fragment 2' was cut. The cutting step (a) is advantageously performed from the incision that has been made.

According to the invention, the arthrodesis method according to the invention also comprises a step (b) of moving the first bone fragment 2' so that at least one portion of its bleeding bone surface 2'B comes into contact with the other bone, referred to as the second bone 3, so as to enable the osteosynthesis of said first bone fragment 2' with said second bone 3. Advantageously, in the step (b) of moving the first bone fragment 2', at least one portion of the bleeding bone surface 2'B of the first bone fragment 2' is placed in contact with the articular surface 3B of the second bone 3, i.e. the surface of the second bone 3 defining the articular slot 4.

As is illustrated in FIG. 1, the cutting step (a) advantageously comprises a phase in which a generally cylindrical bone sample 7 is placed in the first bone 2, wherein said bone sample 7 forms the first bone fragment 2'. In this case, the bleeding bone surface 2'B corresponds to the cut lateral surface of the bone sample 7. The first bone fragment 2', thus cut, advantageously constitutes a bone graft 5 which, appropriately positioned, will provide the arthrodesis of the joint 1.

Advantageously, in the step (a) of cutting the bone sample 7, a generally cylindrical recess 6 is formed, which contains said bone sample 7 (or bone graft 5) (FIGS. 2a and 2b). Unlike the methods of the prior art, the method according to the invention does not comprise a step in which the recess 6 is emptied of its contents, i.e., the first bone fragment 2' is not removed. This then constitutes, as such, the bone graft 5.

According to a particularly advantageous feature of the invention, the movement step (b) involves causing the first bone fragment 2' (or bone sample 7) to turn around within the recess 6, for example, in the direction of rotation R shown in FIG. 2b, with an angle sufficient to enable at least one portion of the bleeding bone surface 2'B of the first bone fragment 2' to be placed opposite the articular surface 3B of the second bone 3.

As is shown in FIG. 1, the recess 6 preferably extends longitudinally according to a longitudinal axis X-X' which is preferably parallel to the axis of the joint 1, i.e. the main axis around which the bones 2, 3 can, in a healthy subject, turn around one another. The movement step (b) thus involves causing the bone graft 5 contained in the recess 6 to turn around, about the longitudinal axis X-X'.

Advantageously, the moving step (b) also involves causing the first bone fragment 2' (or the bone sample 7) to turn, until its articular surface 2'C is no longer opposite the articular surface 3B of the second bone 3. Indeed, the osteosynthesis should preferably occur between bleeding bone surfaces, i.e. free of cartilage. The presence of cartilage can indeed slow and even prevent bone reconstruction, and therefore the fusion between the bones.

Thus, the surgical method according to the invention, and in particular the embodiment shown in FIGS. 1, 2a and 2b, can comprise an additional step of resection of the end 3A of the second bone 3 defining the articular slot 4 in order to remove the damaged bone portions and/or the cartilage that may be present on the articular surface 3B, thus promoting osteosynthesis. This additional step, however, like the methods of the prior art, causes a slight shortening of the limb in which the joint 1 is located.

Figures 4A, 4B:
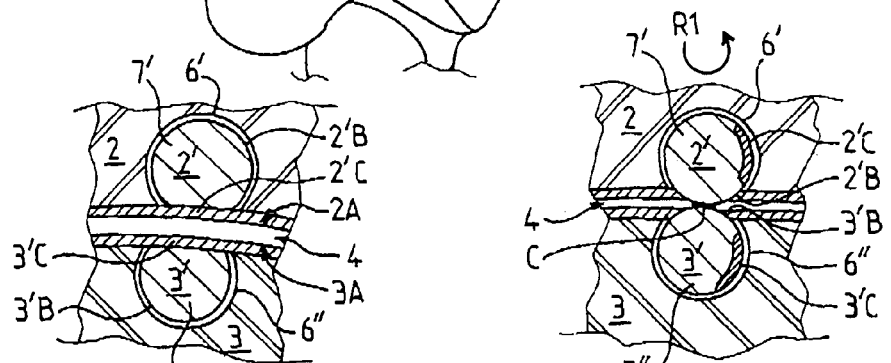
FIGS. 4a and 4b are cross-section detail views showing the bone graft shown in FIG. 3 in a configuration prior to its positioning (FIG. 4a) and in a position, referred to as functional position (FIG. 4b) following its positioning, in which the bone reconstruction is possible.

A preferred alternative embodiment of the invention, which does not cause such a shortening phenomenon, is described below in reference to FIGS. 3, 4a and 4b.

According to this alternative, the cutting step (a) comprises a phase during which a first and a second bone fragment 2', 3' are cut at the ends 2A, 3A, respectively, of the first and second bones 2, 3 defining the articular slot 4, so that the first and second bone fragment 2', 3' each comprise a bleeding bone surface 2'B, 3'B and an articular surface 2'C, 3'C, which, for example, has cartilage and at least partially defines the articular slot 4.

Advantageously, the step (b) of moving the first and second bone fragments 2', 3' includes a phase in which their bleeding bone surfaces 2'B, 3'B are positioned opposite one another. The moving step (b) thus enables the first and second bone fragments 2', 3' to be positioned with respect to one another so as to enable the osteosynthesis between the two bone fragments 2', 3', and the osteosynthesis between each of the bone fragments 2', 3' and the first and second bones 2, 3.

Advantageously, the cutting step (a) comprises a phase in which a first and a second generally cylindrical bone sample 7', 7" are provided so that said first and second bone samples 7', 7" form said first and second bone fragments 2', 3'. In the cutting step (a), a first and a second generally cylindrical recess 6', 6" are thus formed, in which the first and second bone samples 7', 7", respectively, are contained. According to a particularly advantageous aspect of the invention, the moving step (b) involves, according to this alternative, causing the first and second bone samples 7', 7" (or first and second bone fragments 2', 3') to be turned around in their respective recesses 6', 6", for example, in opposite direction of rotation R1, R2, as shown in FIG. 4b, and with an angle sufficient for enabling their respective bleeding bone surfaces 2'B, 3'B to be placed opposite one another.

According to this alternative, and as shown in FIG. 3, the bone fragments 2', 3' (or bone samples 7', 7"), as well as the recesses 6', 6", extend parallel, along the longitudinal axis X-X'. The bone fragments 2', 3' are thus juxtaposed on each side of the articular slot 4. Once placed in their functional position shown in FIG. 4b, the bone fragments 2', 3' in combination advantageously form the bone graft 5, which, by fusion with the first and second bones 2, 3, will enable the arthrodesis of the joint 1. This alternative thus makes it possible to avoid the aforementioned resection step, and therefore does not involve modifying the initial length of the member in which an arthrodesis is performed.

However, the two alternatives described above have a disadvantage insofar as the contact surface C between the first bone fragment 2' and the second bone 3 (alternative shown in FIG. 2b) or between the first and second bone fragments 2', 3' is reduced, and is even further reduced when the bone graft 5 and the bones 2, 3 forming the joint 1 are small. Thus, it can be difficult to obtain a satisfactory fusion if the contact surface C is too small. Indeed, this contact area C can constitute a fragile area capable of resulting in a subsequent break of the bone link between the bones 2, 3, in particular when strong mechanical forces are exerted on the joint 1.

A third, even more preferable, alternative embodiment of the surgical method according to the invention is described below, in reference to FIGS. 5, 6a and 6b.

According to this third alternative, the cutting step (a) includes at least one phase during which a first and a second bone fragment 2', 3' are cut at the ends 2A, 3A of the first and second bones 2, 3 defining the articular slot 4, so as to form a recess 8 (or bone cavity) and to form, in said recess 8, a bone graft 5 constituted by the juxtaposition of the bone fragments 2', 3'. The bone graft 5 thus extends on each side of the articular slot 4, between a first bleeding bone surface 2'B, initially located, i.e. before the moving step (b), substantially opposite the cut surface 2C of the first bone 2, and a second bleeding bone surface 3'B initially located substantially opposite the cut surface 3C of the second bone 3. Thus, the first bleeding bone surface 2'B corresponds substantially to the surface on which the first bone fragment 2' is cut. Similarly, the second bleeding bone surface 3'B corresponds to the surface on which the second bone fragment 3' is cut in step (a). The bone graft 5 is therefore advantageously formed by the first and second bone fragments 2', 3' juxtaposed in the recess 8 and separated by a gap I initially corresponding to the articular slot 4. The articular surfaces 2'C, 3'C of the first and second bone fragments 2', 3', for example, with damaged cartilage, are thus located on each side of the gap I separating the bone fragments 2', 3', and therefore substantially at the centre of the bone graft 5. Obviously, the cut surfaces 2C, 3C of the first and second bones 2, 3 which, according to the invention, correspond to the surfaces for cutting the recess 8 in the bones 2, 3 are advantageously bone surfaces. The cut surfaces 2C, 3C thus coincide with the internal wall 81 of the recess 8.

In the context of the invention, the term "bone surface" refers to a surface formed primarily by bone tissue, as opposed to a cartilaginous surface, formed primarily by cartilaginous tissue.

In the context of the invention, "bone graft" therefore refers to either a single bone fragment 2' or an assembly of bone fragments 2', 3' cut in the joint 1 when creating recesses 6, 6', 6" or 8. The bone graft 5 therefore constitutes a one-piece assembly formed either by a single bone fragment 2' or by a plurality of bone fragments 2', 3' juxtaposed in the recesses 6', 6" or 8.

Preferably, the recess 8 extends longitudinally along a longitudinal axis X-X' preferably parallel to the axis of the joint 1. To implement this cutting step (a), the recess 8 is very specifically formed in the direction in which the ends 2A, 3A of the bones 2, 3 are as planar as possible. This ensures that when the recess 8 is formed, a single bone fragment 2' is cut in the first bone 2, and a single bone fragment 3' is cut in the second bone 3. In practice, if the ends 2A, 3B of the bones 2, 3 have a greater curve, according to a given cutting plane, the recess 8 is preferably formed so that its longitudinal extending direction is substantially perpendicular to the aforementioned cutting plane.

According to this third alternative, the moving step (b) comprises a phase in which the bone graft 5 is moved in the recess 8 so that at least one portion of the first bleeding bone surface 2'B is substantially opposite the cut surface 3C of the second bone 3, and at least one portion of the second bleeding bone surface 3'B is opposite the cut surface 2C of the first bone 2, so as to enable the osteosynthesis of said first and second bone fragments 2', 3' with said second and first bones 3, 2, respectively.

The cutting step (a) preferably includes a phase in which a generally cylindrical bone sample 7, which forms the bone graft 5, is provided.

Figures 6A, 6B:
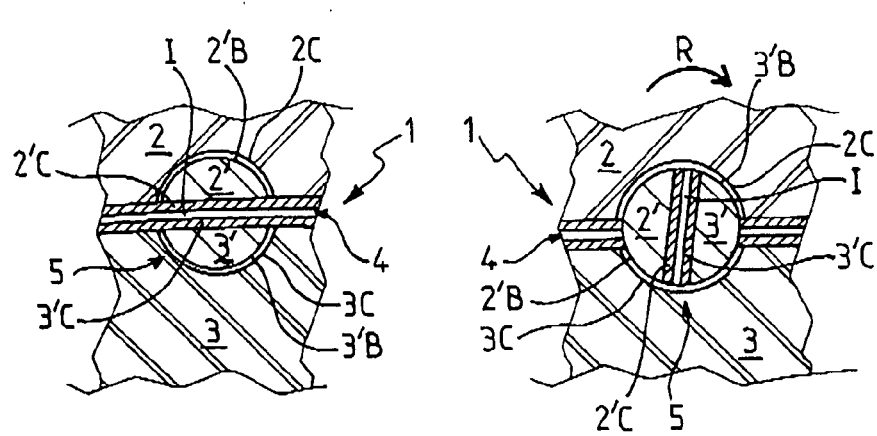
FIGS. 6a and 6b are cross-section detail views showing the bone graft shown in FIG. 5 in a configuration following the cutting step but prior to the positioning (FIG. 6a) and a so-called functional configuration (FIG. 6b), following the positioning step, in which the osteosynthesis between the bone graft and the bones forming the joint can take place.

In a particularly advantageous manner, the moving step (b) involves causing the bone graft 5 to turn around in the recess 8, for example, in a direction of rotation R shown in FIG. 6b, and with an angle sufficient to enable at least one portion of the first and second bleeding bone surfaces 2'B, 3'B to be placed opposite the cut surfaces 3C, 2C, respectively, of the second and first bones 3, 2. Thus, in the moving step (b), the bone graft 5 is preferably made to turn about 90° with respect to its initial position, i.e. substantially a quarter turn, as shown in FIG. 6b. In this configuration, which constitutes the functional configuration of the bone graft 5, in which the osteosynthesis can take place, the gap I extends in a direction substantially perpendicular to the articular slot 4 and the contact area between the different bone surfaces is optimal for ensuring proper bone reconstruction.

In each of the aforementioned alternatives, it should be noted that the material necessary for the osteosynthesis (or "bone fusion") is formed and then used in situ, that is, the bone graft 5 can advantageously be the local product of the shaping of the recess (6, 6', 6", 8) rather than being transplanted.

Removing the material necessary for constructing he arthrodesis support directly from the joint involved in the treatment advantageously makes it possible to eliminate the steps of removing and transplanting a graft, for example, from a trephining operation preformed on the patient's iliac crest, as is usually done in the prior art.

This simplification of the surgical procedure also limits the trauma experienced by the patient, as well as the risk of intraoperative errors and/or post-operative complications.

To further accelerate the bone reconstruction, the surgical method according to the invention can also include, after the moving step (b), a compression step (c), in which radial expansion of the bone graft 5 is caused in order to improve the contact between the first and second bleeding bone surfaces 2'B, 3'B and the cut surfaces 3C, 2C of the first and second bones 3, 2.

This compression step (c) thus advantageously includes a phase in which a compression member 9, such as a wedge, is inserted into the gap I so as to separate the first and second bone fragments 2', 3' from one another and to push them against the internal wall 81 of the recess. This compression step (c) thus involves a phase of external radial or centrifugal compression of the bone fragments 2', 3' according to the arrows F shown in FIG. 7. Preferably, the enough compression is exerted to ensure the immobilisation of the bone graft 5 in the recess 8, by friction on the internal wall 81 thereof. Depending on the mechanical properties of the materials constituting the tissues and the compression member, the compression may be accompanied by a substantially pronounced local deformation of the elements forming the graft 5, the recess 6, 6', 6", 8 and/or the compression device.

Figure 7:
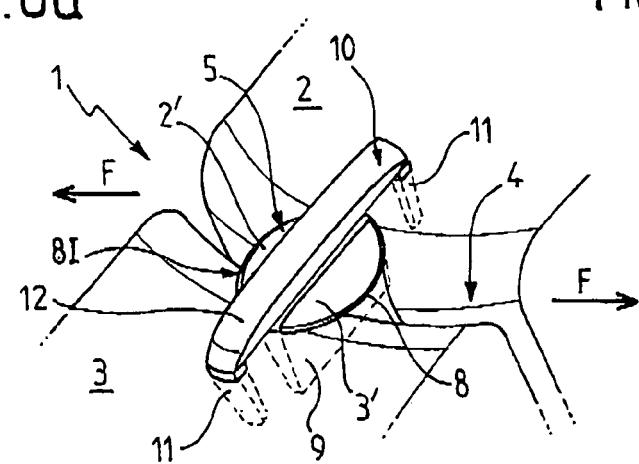
FIG. 7 is a perspective view showing a detail of the joint with a bone graft located between the bones located on each side of an articular slot and attached with a suitable attachment means.

The surgical method according to the invention also includes, after the moving step (b), and optionally the compression step (c), a step (d) of locking the bone graft 5 in position with respect to the first and second bones 2, 3, using a suitable attachment means 10, so as to ensure the arthrodesis of the joint 1. The locking step (d) clearly applies to all of the embodiments described above, whether the bone graft 5 is formed by a single bone fragment or by several bone fragments 2', 3'. The attachment means 10 can advantageously include two anchoring elements 11, connected by a connection element 12, wherein said anchoring elements 11 are intended to be inserted, for example, by percussion or hammering, using an impactor, into the first and second bones 2, 3, so as to ensure their relative immobilisation (FIG. 7).

The compression (c) and locking (d) steps are preferably performed simultaneously using a single attachment means 10 provided with a compression member 9. Therefore, the method according to the invention makes it possible, by using a bone graft 5 cut from the joint 1, to avoid using a transplant and therefore reduces the risk of operative and post-operative complications.

This invention, in association with the aforementioned arthrodesis method, also relates to an ancillary device 20 for positioning the bone graft 5 between the first and the second bone 2, 3. The ancillary positioning device 20 is advantageously suitable for moving the bone graft 5, whether the latter is formed by a single bone fragment or by several bone fragments, and in particular two bone fragments 2', 3'. In this latter case, the bone graft 5 can be moved in either a single movement, by moving the bone fragments 2', 3' juxtaposed in the same recess 8, or in separate movements, by moving the bone fragments 2', 3' separately in their respective recesses 6', 6".

According to the invention, and as is shown in FIG. 5, the ancillary device 20 includes a means 21 for driving the bone graft 5, provided with support means 22 on said bone graft 5 suitable for moving the latter in the recess 8. The ancillary device 20 in this case is represented in association with a bone graft 5 formed by the juxtaposition of two bone fragments 2', 3'. However, the ancillary device 20 according to the invention can clearly be used to move a bone graft 5 formed by a single bone fragment 2', such as that shown in FIG. 1.

According to the invention, the ancillary device 20 also includes actuation means 23, functionally connected to the driving means 21, and capable of being handled, in particular by the surgeon, for controlling the movement of the bone graft 5.

In a particularly advantageous manner, the ancillary device 20 is suitable for rotating the bone graft 5 in the recess 6, 6', 6", 8 so as to ensure its proper positioning. The driving means 21 are thus advantageously mounted on the bone graft 5 with a possibility of rotating with respect to the first and second bones 2, 3. More specifically, the driving means 21 are preferably mechanically connected to the actuation means 23 so that a rotation movement of the actuation means 23 causes a rotation movement of the driving means 21.

Even more preferably, the actuation means 23 and the driving means 21 are arranged so as to turn simultaneously with the same angular amplitude.

Figure 8:
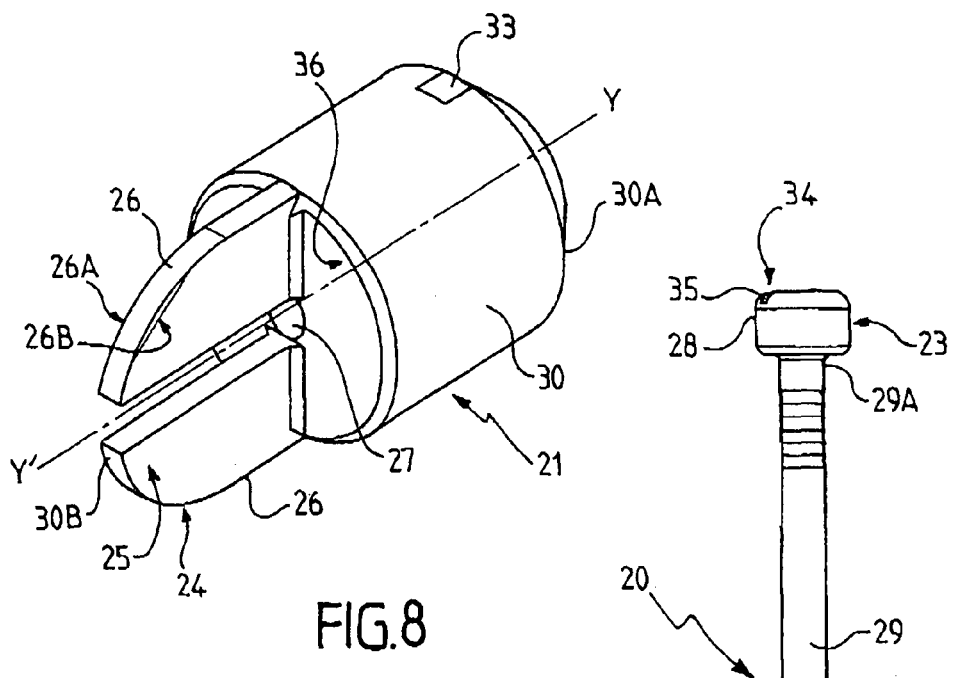
FIG. 8 is a perspective view showing a detail of the means for driving the ancillary positioning device according to the invention.
Figures 9, 10:
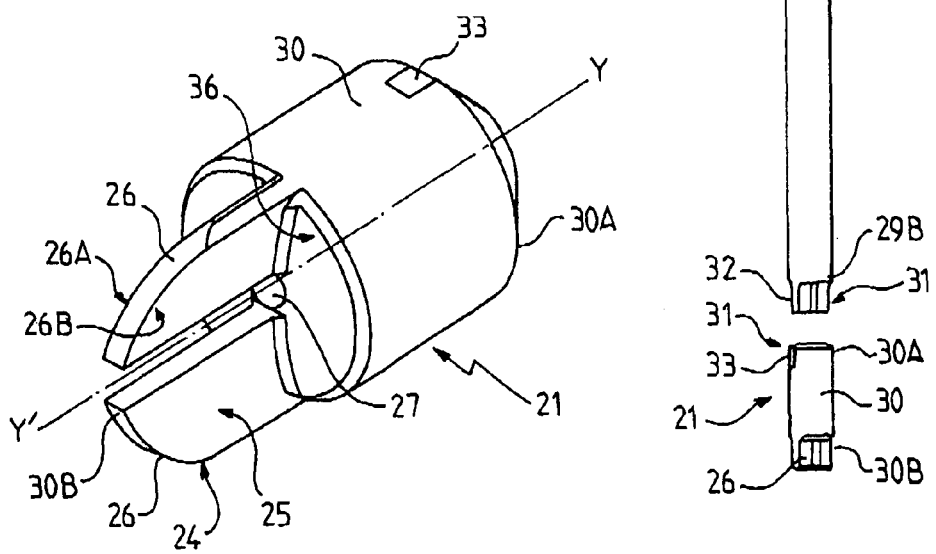
FIG. 9 is a perspective view showing an anatomical alternative of the driving means according to the invention.
FIG. 10 is a cutaway perspective view showing a detail of the ancillary positioning device according to the invention.

According to a particularly advantageous feature of the invention, and as is shown in FIGS. 8 and 9, the driving means comprise a penetration member 24 suitable for being inserted into the bone graft 5 along the longitudinal axis X-X' of extension of the recess 6, 6', 6", 8. The penetration member 24 advantageously bears support means 22 that can, for example, be formed by a plurality of pins (not shown), for example, three pins arranged in a triangle, intended to penetrate the inside of the bone fragments 2', 3' in order to ensure the rotation of the bone graft 5. More preferably, the support means 22 are formed by at least one contact surface 25, arranged on the penetration member 24, and intended to come into contact with the bone graft 5 (or the bone fragments 2', 3') in order to drive the latter in rotation in the recess 6, 6', 6", 8 and about the longitudinal axis X-X'.

In a particularly advantageous manner, the penetration member 24 can have a tapered end so as to facilitate its insertion into the bone graft 5, in particular when the latter is formed by a single one-piece bone fragment.

According to a preferred embodiment particularly suitable for the case in which the bone graft 5 is formed by the juxtaposition of two bone fragments 2', 3' arranged in the recess 8 and separated by a gap I, the penetration member 24 is preferably formed by at least one substantially rigid blade 26, shaped so as to be inserted into the articular slot 4 (or into the gap I separating the first and second bone fragments 2', 3').

The blade 26 advantageously has two opposite surfaces 26A, 26B, each being suitable for coming into contact with at least one of the bone fragments 2', 3', in order to drive the bone graft 5 in rotation.

According to a first alternative shown in FIG. 8, the blade 26 is substantially planar. According to a preferred alternative shown in FIG. 9, the blade has an anatomical shape with a substantially curved cross-section so as to fit, with a small clearance, the shape of the gap I (or of the articular slot 4). More specifically, the blade 26 thus substantially fits the shape of the articular surfaces 2'C, 3'C of the first and second bones 2, 3. This configuration of the blade 26 enables it to come into close contact with the bone fragments 2', 3', thus improving the precision of the positioning of the bone graft 5.

The conformation of the component of the driving means 21, the support means 22 and the penetration member as described above advantageously enables the engagement with the graft 5 to be ensured and said graft 5 to be handled in various ways, whether it is flush, recessed or projecting with respect to the adjacent external surface of the joint 1 in which the recess is formed (6, 6', 6", 8).

In order to facilitate the positioning of the ancillary device 20 with respect to the joint 1, the surgeon generally uses a centering pin (not shown) intended to be inserted, by one of its ends, into the articular slot 4, so that the centering pin extends parallel to the longitudinal axis X-X'. In this way, the penetration member 24 advantageously comprises a substantially central aperture 27, enabling the pin to pass through, which extends longitudinally in the longitudinal direction Y-Y' of extension of the driving means 21, with the longitudinal direction Y-Y' substantially merging with the longitudinal axis X-X' when the penetration member 24 is inserted into the articular slot 4 (or the gap I).

According to an even more preferable alternative of the invention shown in FIGS. 8 and 9, the penetration member 24 is advantageously formed by two blades 26 arranged in alignment on each side of the aperture 27. This makes it possible in particular to ensure proper contact between the penetration member 24 and the bone fragments 2', 3', while enabling the ancillary device 20 to be centered with a centering pin.

The actuation means 23 preferably comprise a gripping member 28, such as a wheel, as well as a rod 29 extending between the gripping member 28 and the driving means 21 in order to connect the latter mechanically.

The rod 29 is preferably rigidly connected, and for example attached to or integrated with the gripping member 28 so that when a rotation movement is imparted on the gripping member 28, it simultaneously drives the rod 29 in the same rotation movement.

According to a preferred alternative of the invention, the driving means 21 is formed by an end piece 30 that is removable, i.e. separated, from the rod 29 and intended to cooperate with it. Thus, the rod 29 extends longitudinally between a proximal end 29A, connected to the gripping member 28, and a free distal end 29B to which the driving means 21 are advantageously intended to be connected. In this way, the end piece 30 and the rod 29 are advantageously provided with mutual cooperation means 31, for example, formed by a lug 32, preferably placed at the distal end 29B of the rod 29, and a corresponding notch 33, preferably provided on the end piece 30, precisely at the proximal end 30A of the end piece 30, opposite the distal end 30B forming the penetration member 24 (FIG. 10).

In order to make it easier to locate the position of the bone graft 5 and more specifically the position of the gap I with respect to the articular slot 4, the ancillary device 20 advantageously comprises a means 34 for viewing the angular positioning of the bone graft 5, which viewing means 34 are preferably connected to the driving means 21 so as to indicate the angular position thereof.

The viewing means 34 should thus enable the surgeon to control the movement of the bone graft 5 in its recess 6, 6', 6", 8, in particular the angular amplitude of movement, and to verify that the bone graft 5 is indeed in its functional position, once this movement has been performed.

To this end, the viewing means 34 are preferably formed by a reference point such as a groove 35 on the gripping member 28 which preferably extends parallel to the blade 26 (FIG. 10). Thus, when the penetration member 24 is inserted into the articular slot 4 or the gap I between the bone fragments 2', 3', the viewing means 34 indicate precisely the position of the gap I and therefore the positioning of the bone graft 5 in the recess 6, 6', 6", 8.

According to a preferred embodiment shown in FIGS. 11, 12 and 13, the ancillary device 20 advantageously comprises cutting means 40 comprising a substantially cylindrical hollow tube 41 extending between a proximal end 41A and a distal end 41B, and provided at its distal end 41B with preparation means 42 suitable for forming the recess 6, 6', 6", 8 in the joint 1. Preferably, the preparation means 42 are formed by a series of teeth 43, with the cutting means 40 forming a cylinder saw (or circular saw). The cutting means 40 are advantageously associated with a motor, by means of a mandrel (not shown) in order to drive the cutting means 40, and specifically the trephine, in rotation.

According to a particularly advantageous feature of the invention, the ancillary device 20 also comprises means for guiding the bone graft 5 in rotation in the recess 6, 6', 6", 8, which enable the bone graft 5 to be properly positioned while limiting the risk of damaging or breaking the bone graft 5. In a particularly advantageous manner, the rotational guide means are formed by the tube 41 of the cutting means 40, which is left in place in the recess 6, 6', 6", 8 after the cutting step (a).

According to yet another advantageous feature, which constitutes a separate invention, the ancillary device 20 comprises an instrument 50 for extracting the cutting means 40, suitable for extracting the latter from the recess 6, 6', 6", 8, once the bone graft 5, and in particular the bone fragments 2', 3' have been cut.

The ancillary device 20 can thus advantageously comprise the driving means 21, the actuating means 23 and the extraction instrument 50, but can also be formed by the extraction instrument 50 alone, which forms a separate invention.

Advantageously, the extraction instrument comprises at least one driving element 51 suitable for cooperating with the cutting means 40 for extraction of the latter, and preferably at least one means for holding the bone graft 5 suitable for coming into contact with the bone graft 5 in order to hold the latter in the recess 6, 6', 6", 8 when the cutting means 40 is extracted. The holding means are thus advantageously suitable for preventing, during extraction of the cutting means, the simultaneous removal of the bone graft 5 capable of being locked in the tube 41.

Advantageously, the extraction instrument 50 also includes at least one base 52 on which the driving element 51 is translatably mounted. The base 52 thus advantageously comprises a first hollow cylinder 53, in which the driving element 51 is mounted, preferably formed with a second cylinder that is axially slidably mounted in the first cylinder 53.

According to a particularly advantageous feature of the invention, the holding means are formed by the association of the driving means 21, which come into contact with the bone graft 5 by means of a bearing surface 36, substantially perpendicular to the blade 26, and the rod 29, which is rigidly connected to the base 52 by means of a suitable attachment member 67, such as a butterfly screw.

According to a particularly advantageous feature of the invention, the extraction instrument 50 also comprises at least one control member 60 rotatably mounted with respect to the base 52. The base 52 thus includes, a support element 55 advantageously secured to the first cylinder 53, on which the control member 60 is mounted with a possibility of pivoting. The support element 55 thus extends perpendicularly with respect to the first cylinder 53 and comprises a central hole 55A capable of receiving the first cylinder 53.

The control member 60 is thus advantageously mounted so as to move between a pre-extraction position, referred to as the first position (shown in FIG. 11) and a post-extraction position, referred to as the second position (shown in FIG. 12).

In the first position, the cutting means 40 are in a low position, i.e. they are still located in the recess 6, 6', 6", 8 after cutting the bone graft 5. However, in the second position, the cutting means 40 are located in the high position, i.e. they are located outside the recess 6, 6', 6", 8.

Thus, the control member 60 is advantageously functionally, and preferably mechanically, connected to the driving element 51 so as to direct the movement thereof.

The driving element 51 thus extends between a proximal end 51A, provided with at least one guide pin 57 intended to cooperate functionally with the control member 60, and a distal end 51B connected to the cutting means 40, for example, by means of a clip system 58 (FIG. 13). The first cylinder 53 is thus advantageously suitable for receiving the driving element 51 and therefore comprises at least one longitudinal slot 56 suitable for receiving the guide pin 57 so that the latter can slide along said longitudinal slot 56.

To reduce the movement of the driving element 51, the control member 60 advantageously includes at least one extraction rail 61 shaped so as to engage the guide pin 57 and to exert a thrust on the latter when the control member 60 turns, in a direction of rotation Q shown in FIG. 11, from its first position (FIG. 11) to its second position (FIG. 12). The rotation of the control member 60 then causes the translation of the driving element 51 in a first direction F1 and the removal of the cutting means 40 from the recess 6, 6', 6", 8.

In a particularly advantageous manner, the control member 60 also comprises at least one resetting rail 62 which enables the configuration of the extraction instrument 50 to be reset so as to prepare it for a new use. The resetting rail 62 is advantageously designed so as to engage the guide pin 57 and to exert a thrust on the latter when the control member 60 turns from its second position to its first position, thus causing the translation of the driving element 51 in a second direction F2 (FIG. 12) opposite the first direction F1, and the resetting of the extraction instrument 50 for a new use.

Even more preferably, the control member 60 comprises at least one groove 63, the edges of which form the rails for extraction 61 and resetting 62. The guide pin 57 is then guided in movement along said groove 63.

Advantageously, the control member 60 comprises at least one control arm 64 mounted on the base 52 with a possibility of rotation, and on which said groove 63 is formed. The control arm 64 thus advantageously comprises an external surface 64A and an internal surface 64B on which the groove 63 is formed. More specifically, the control arm 64 is mounted with a pivot link on the support element 55 of the base 52.

According to a preferred alternative shown in FIGS. 11 and 12, the control member 60 preferably comprises two control arms 64, 65 mounted symmetrically on the base 52 on each side of the first cylinder 53 so as to move symmetrically with respect to the longitudinal axis of extension of the first cylinder 53.

Each control arm 64, 65 advantageously has, at one of its ends, an engagement zone E designed so as to facilitate the engagement between the guide pin 57 and the extraction rail 61 or the groove 63.

The control member 60 advantageously also comprises at least one gripping handle 66, located in the extension of the control arm 64, 65 so as to enable its manipulation. Obviously, if the control member 60 comprises two control arms 64, 65, it will also comprise two corresponding gripping handles 66 preferably placed at the ends of the control arms 64, 65 opposite the engagement zone E.

It is also possible to consider providing the extraction instrument 50 and in particular the control member 60 with resilient return means (not shown) suitable for exerting on the control arms 64, 65 a return stress causing them to return to the pre-extraction configuration shown in FIG. 11. These resilient return means thus ensure the automatic resetting of the extraction instrument 50.

The placement and operation of the positioning element 30 according to the invention are described below in reference to FIGS. 1 to 13.

Before proceeding with the cutting of the bone fragments 2', 3' forming the bone graft 5, the surgeon must first measure the depth of the joint to be treated in order to ensure that the cut of the bone graft 5 (or the bone sample 7) is of the appropriate length, substantially corresponding to the depth of the joint 1.

In particular, in the cutting step, the cutting means 40 should be prevented from going beyond the external surface 70 of the joint and from damaging the soft tissue, and even the joints or the other bones located behind the joint 1 to be treated.

The measurement of the joint 1 is performed using a hook (not shown) intended to be placed against the external surface 70 of the joint 1, which hook is associated with a rule for measuring the depth.

Before making the cut in the bones 2, 3 forming the joint 1, the surgeon then adjusts the depth derived from the measurement taken in the first step mentioned above on a telescopic protection cylinder (not shown). This protection cylinder, comprising, for example, two cylinders sliding one inside the other and held together by a radial set screw, is intended to form a adjustable stop preventing the cutting means 40 from penetrating the joint 1 beyond the predetermined depth. The protection cylinder therefore ensures the safety of the cut.

Prior to the cutting step, the surgeon inserts, in the articular slot 4, precisely where the recess is to be formed 6, 6', 6", 8 and the bone graft 5 is to be cut, the penetration member 24, in particular the blade 26 of the end piece 30 separated from the rod 29. The end piece 30 performs a centering function for the trephine by representing the position of the cutting tool axis. Advantageously, the position of the notch 33 made in the same plane as the blade 26 reflects the angular position of said blade 26 along the axis XX' and thus enables the precise position of the bone graft 5 to be known once the latter has been cut.

The surgeon can then attach the cutting means 40, for example the trephine, to a mandrel which will be engaged with a motor (or motor reducer) in order to drive the cutting means 40 in rotation and to cut the bone sample 7 forming the bone graft 5.

Advantageously, the powered driving device can include a disconnection system or a torque limiter which will cooperate with the depth stop so as to stop the cutting by automatically disconnecting said device from the trephine once the desired depth has been reached.

Once the bone sample 7 is obtained, the surgeon uses the remainder of the ancillary device 20 to turn it. Thus, it is in particular the assembly consisting of the extraction device 50, in particular its base 52, the driving means 21, the cutting means 40 and the graft 5 which will be manually oriented by the surgeon so as to place the graft in the most favourable position for arthrodesis. To this end, the elements are preferably temporarily rigidly connected at their axis of rotation XX' by means of a suitable assembly.

As necessary, the ancillary device may in particular be controlled so that the viewing means 34 show that the blade, and therefore plane of extension of the gap I is substantially orthogonal to the plane of the initial articular slot 4.

The surgeon thus first mounts the driving element 51 formed by the second internal cylinder 54 on the cutting means 40, by attaching it, for example, using a clip system 58.

The surgeon then mounts the first hollow cylinder 53 on the second cylinder 54 so that it surrounds said second cylinder 54, thus forming an external cylinder. The medical practitioner then places the first cylinder 53 against the bones 2, 3 defining the recess 6, 6', 6", 8, outside the cut area. The first cylinder 53 thus comes into contact with the periphery of the recess 6, 6', 6", 8 by means of its distal end 53A.

It should thus be noted that the cylinder 53 advantageously performs the role of an extraction stop that will hold the bones 2, 3 in place during extraction of the cutting means 40 and provide the support, in particular axial support, necessary for moving said cutting means 40 with respect to the recess 6, 6', 6", 8.

The surgeon then inserts the actuating means 23, equipped with the viewing means 34, inside the second cylinder 54. Owing to the notch 33 made on the proximal end 30A of the end piece 30 and the lug 32 formed on the corresponding end of the rod 29, the surgeon can easily cause the actuating means 23 to merge with the driving means 21, in particular by trial and error. By thus determining, with the groove, the orientation of the plane of extension of the gap I, the surgeon can also easily identify any movement (for example, an angular shift) of the bone graft 5, following the cutting step.

Advantageously, the cutting means 40, in particular the trephine, remain in position inside the recess 6, 6', 6", 8 so as to form means for guiding the bone graft 5 in rotation. The surgeon can then find the initial position of the bone graft 5, in which the gap I is substantially in alignment with the articular slot 4. Once the initial position has been found, the surgeon attaches the rod 29 to the base 52, precisely on the support element 55 using the attachment member 67 (butterfly screw, for example). The rod 29 and the driving means 21 are then attached to the base 52.

In fact, the graft 5 is then rotatably connected with respect to the axis XX' of the ancillary device 20.

Once this step has been performed, the surgeon searches for the optimal position of the bone graft 5 enabling good bone reconstruction, and can thus turn the ancillary positioning device 20 a quarter turn, so that the blade 26 is substantially perpendicular to the articular slot 4. In this configuration, the gap I separating the bone fragments 2', 3' is substantially perpendicular to the articular slot 4, as shown in FIG. 6b.

Once the bone graft 5 has been properly positioned in its recess 6, 6', 6", 8, the ancillary positioning device 20 and in particular the cutting means 40 should be removed, while making sure at the same time not to remove the bone graft 5 which is capable of being locked in the tube 41.

To this end, the surgeon moves the handles 66 of the extraction instrument 50, turning them in a direction of rotation Ω shown in FIG. 11, so that the handles are substantially perpendicular to the first cylinder 53. As the control arms 64, 65 are rotated, the guide pin 57 slides along the longitudinal slot 56 of the first cylinder 53, causing the driving element 51 and the cutting means 40 to which it is attached to move up.

At the same time, the rod 29 and the driving means 21, still attached to the base, come into contact with the bone graft 5, and in particular the bone fragments 2', 3' by means of the bearing surface 36 of the end piece 30. Thus, the bone graft 5 is substantially held in place in its recess while the cutting means 40 is urged by a relative extraction movement.

Once the ancillary positioning device 20 has been removed, the surgeon can set the bone graft 5 in its functional position, using the attachment means 10.

The surgical method and the ancillary positioning device 20 according to the invention therefore enable the cutting and positioning of the bone graft 5 to be performed by a synergistic combination of means in a minimum number of steps, without the risk of damage, and minimizing the risk of operation errors.

The invention claimed is:

1. A method for arthrodesis of a joint between at least two bones separated by an articular slot, said at least two bones having ends and defining said articular slot, said method comprising the steps of:

Cutting in situ at least one first bone fragment at an end of one of said at least two bones, said end of one of said at least two bones, referred to as the first bone, so that the first bone fragment has a bleeding surface and an articular surface with said articular surface at least partially defining the articular slot; and Moving in situ the first bone fragment so that at least one portion of its bleeding surface comes into contact with a second bone of said at least two bones, referred to as the second bone, so as to enable osteosyntheis of said first bone fragment with said second bone.

2. The method according to claim 1, in which said second bone has an articular surface (3B), and wherein during the moving step, at least one portion of the bleeding bone surface (2'B) of the first bone fragment is placed opposite the articular surface (3B) of the second bone.

3. The method according to claim 1, wherein the cutting step includes a phase of providing a generally cylindrical bone sample (7) in the first bone, said generally cylindrical bone sample forming said first bone fragment.

4. The method according to claim 3, wherein during the cutting step, a generally cylindrical recess (6) is formed, in which the bone sample is contained (7).

5. The method according to claim 4, in which said second bone has an articular surface, and wherein the moving step involves causing said bone sample to turn around in said recess according to an angle sufficient for enabling at least one portion of the bleeding bone surface to be placed opposite the articular surface of the second bone.

6. The method according to claim 5, wherein the bone sample is caused to turn until its articular surface (2'C) is no longer opposite the articular surface (3B) of the second bone.

7. The method according to claim 1, wherein the second bone (3) has an end (3A) having cartilage and/or damaged bone portions, said method further comprising a step of resectioning said end (3A) of the second bone defining the articular slot in order to remove the cartilage and/or the damaged bone portions.

8. The method according to claim 1, further comprising the steps of cutting a second bone fragment at an end of the second bone, such that the second bone fragment also comprises a bleeding bone surface and an articular surface which at least partially defines the articular slot; and Moving the first and second bone fragments so as to place the respective bleeding bone surfaces opposite one another.

9. The method according to claim 8, wherein the articular slot has a longitudinal axis (XX') and wherein the cutting step further comprises a phase in which a first (7') and a second (7") generally cylindrical bone sample are provided, wherein said first and second bone samples form said first and second bone fragments (2', 3') and extend parallel to one another, along the longitudinal axis (XX').

10. The method according to claim 9, wherein during the cutting step, a first (6) and a second (6") generally cylindrical recess are provided, in which the first and second bone samples, respectively, are contained, and which extend parallel to one another, along the longitudinal axis (XX').

11. The method according to claim 10, wherein the moving step involves causing said first and second bone samples to turn around in their respective recesses according to an angle sufficient to enable their respective bleeding bone surfaces to be placed opposite one another.

12. Simultaneously cutting the first bone fragment at the end of the first bone and a second bone fragment at an end of the second bone so as to form a recess and a cut surface of said first bone and a cut surface of said second bone, and in said recess, a bone graft constituted by a juxtaposition of the first and second bone fragments, wherein the bone graft extends on each side of the articular slot, between a first bleeding surface, located opposite the cut surface of said first bone, and a second bleeding surface, located opposite the cut surface of said second bone; and Moving the bone graft in said recess so that at least one portion of the first bleeding surface is opposite the cut surface of said second bone, and at least one portion of the second bleeding bone surface is opposite the cut surface of said first bone, so as to enable osteosynthesis of said first and second bone fragments with said second and first bones, respectively.

13. The method according to claim 12, wherein the cutting step further comprises a phase in which a generally cylindrical bone sample (7), which forms said bone graft (5) is formed.

14. The method according to claim 12, wherein the moving step involves causing the bone graft (5) to turn around in the recess (8) according to an angle sufficient to enable the first and second bleeding bone surfaces (2'B, 3'B) to be placed opposite the cut surfaces of the second and first bones (3C, 2C), respectively.

15. The method according to claim 12, wherein during the moving step, the bone graft is turned substantially one quarter turn.

16. The method according to claim 12, further comprising a compression step (c) for causing radial expansion of the bone graft (5) in order to improve the contact between the first and second bleeding bone surfaces and the cut surfaces of the first and second bones.

17. The method according to claim 16, wherein said recess has an internal wall (8I'), and wherein the compression step is adequate to ensure that the bone graft (5) is immobilized by friction on the internal wall of the recess.

18. The method according to claim 16, further comprising, after the moving step, a step of locking the bone graft (5) in position with respect to the first and second bones (2, 3), using a suitable attachment means (10), so as to ensure arthrodesis of the joint.

19. The method according to claim 18, in which an attachment implant (10) is provided for effecting the compression step and the locking step, and wherein the compression and locking steps are performed simultaneously, using the same attachment implant (10).

20. The method according to claim 1, further comprising a step of inserting driving means (21) in the articular slot (4), wherein said driving means (21) are provided with support means (22) suitable for moving the first bone fragment.

21. The method according to claim 20, further comprising a step of centering cutting means (40), which are suitable for performing the cutting step, on the driving means (21) inserted in the articular slot (4).

22. The method according to claim 1, wherein the cutting step is performed with an ancillary device (20) provided with cutting means (40) comprising a substantially cylindrical hollow tube (41), so as to form a generally cylindrical recess (6, 6', 6", 8) containing the first bone fragment (2'), wherein said tube (41) is left in place in said recess after said cutting step so as to form means for guiding said first bone fragment in rotation during the moving step.

23. The method according to claim 22, further comprising a step of inserting driving means (21) in the articular slot (4), wherein said driving means (21) are provided with support means (22) suitable for moving the first bone fragment, the method further comprising a step of temporarily connecting said driving means (21) together with the cutting means (40), so as to enable the surgeon to rotate the bone fragment in turning the ancillary device (20) during the moving step.

24. The method according to claim 22, further comprising a step of extracting the cutting means, wherein the bone fragment is held in place in the recess by holding means coming into contact with said bone fragment while the cutting means is urged by a relative extraction movement.

* * * * *